(12) United States Patent
Pluta et al.

(10) Patent No.: US 9,863,900 B2
(45) Date of Patent: Jan. 9, 2018

(54) PLANAR SENSOR ARRAY FOR NON-DESTRUCTIVE EVALUATION OF MATERIAL USING ELECTROMAGNETIC IMPEDANCE

(71) Applicant: TransTech Systems, Inc., Schenectady, NY (US)

(72) Inventors: Sarah E. Pluta, Scotia, NY (US); Donald D. Colosimo, Saratoga Springs, NY (US); John W. Hewitt, Niskayuna, NY (US)

(73) Assignee: TransTech Systems, Inc., Latham, NY (US)

( * ) Notice: Subject to any disclaimer, the term of this patent is extended or adjusted under 35 U.S.C. 154(b) by 390 days.

(21) Appl. No.: 14/605,597

(22) Filed: Jan. 26, 2015

(65) Prior Publication Data

US 2015/0212026 A1    Jul. 30, 2015

Related U.S. Application Data

(60) Provisional application No. 61/932,400, filed on Jan. 28, 2014.

(51) Int. Cl.
    *G01R 25/00*     (2006.01)
    *G01N 27/02*     (2006.01)

(52) U.S. Cl.
    CPC .................................. *G01N 27/02* (2013.01)

(58) Field of Classification Search
    CPC ....................................................... G01N 2/02

USPC ........................................................... 702/65
See application file for complete search history.

(56) References Cited

U.S. PATENT DOCUMENTS

| | | |
|---|---|---|
| 5,900,736 A | 5/1999 | Sovik et al. |
| 6,400,161 B1 | 6/2002 | Geisel |
| 6,414,497 B1 | 7/2002 | Sovik et al. |
| 7,219,024 B2 | 5/2007 | Garnache et al. |
| 2002/0070677 A1* | 6/2002 | Yamada ................ H01J 1/3048 315/169.4 |
| 2005/0263696 A1* | 12/2005 | Wells .................... H01J 49/423 250/292 |
| 2009/0117571 A1* | 5/2009 | Solanki .............. G01N 33/5438 435/6.11 |
| 2009/0170756 A1 | 7/2009 | Burnett, Jr. et al. |
| 2010/0308218 A1* | 12/2010 | Wang ................... H01J 49/063 250/292 |
| 2012/0013354 A1 | 1/2012 | Bowler et al. |
| 2012/0130212 A1 | 5/2012 | Pluta et al. |

\* cited by examiner

*Primary Examiner* — Long K Tran
(74) *Attorney, Agent, or Firm* — Hoffman Warnick LLC (57) ABSTRACT

Various embodiments include planar sensor arrays for use in determining characteristics of a material under test (MUT). The planar sensor arrays can include a set of electrodes positioned to enhance a depth and clarity of detection into the material under test. Some embodiments include an electromagnetic sensor array having: a first set of two rectilinear electrodes, positioned opposed to one another across a space; and a second set of two rectilinear electrodes, positioned opposed to one another across the space, the second set being off-set from the first set, wherein the first set and the second set are configured to detect an electromagnetic impedance of the MUT.

12 Claims, 10 Drawing Sheets

PLANAR SENSOR ARRAY FOR NON-DESTRUCTIVE EVALUATION OF MATERIAL USING ELECTROMAGNETIC IMPEDANCE

CROSS-REFERENCE TO RELATED APPLICATION

This application claims priority to U.S. Provisional Patent Application No. 61/932,400, which is hereby incorporated by reference in its entirety.

TECHNICAL FIELD

Various embodiments of the invention relate to planar sensor arrays for use with electromagnetic impedance sensors to non-destructively evaluate the physical properties of materials under test (MUT). The designs of the sensor array may enhance the depth of measurement into the MUT within a defined sensor size, and may enhance the signal-to-noise ratio.

BACKGROUND

The use of electromagnetic impedance measurement devices to secure physical properties of a material under test with a planar electrode sensor array have been identified in U.S. Pat. Nos. 5,900,736, 6,400,161, 6,414,497, and 7,219,024, each of which is hereby incorporated by reference in its entirety. The apparatus covered in U.S. Pat. Nos. 5,900,736, 6,414,497, and 7,219,024, use a planar concentric electrode array to secure data about a MUT. US Patent Publication No. 2012/0013354 (hereby incorporated by reference in its entirety) also presents a planar concentric electrode array and terms it a "concentric coplanar capacitive sensor". The planar concentric electrode arrays fall under a class of electronics that is termed "coplanar wave guides." While there are a number of advantages in using the concentric electrode array, this array also has limitations. A first limitation is that the concentric electrode array is not readily conducive to providing tomographic information. The use of electromagnetic magnetic tomographic and spectrographic measurement devices, which have been identified in US Patent Publication Nos. 2009/0170756 and 2012/0130212 (each of which is hereby incorporated by reference in its entirety), and U.S. Provisional Patent Application Nos. 61/647,848 and 61/703,488 (each of which is hereby incorporated by reference in its entirety), address the issue of locating specified volumes within an MUT and characterizing that volume based upon its electromagnetic characteristics. A second limitation of the concentric electrode array is that the size of the electrode array limits the potential depth of evaluation into the MUT. In general, the maximum depth that can be evaluated is at best equal to one half of the sensor diameter, and in practice, the depth is even less.

The embodiments of the designs for the planar electrode array presented in the application provide for a means to address the second limitations. The art presented in US Patent Publications 2009/0170756 and 2012/0130212 and Applications 61/647,848 and 61/703,488 address the first limitation.

SUMMARY OF THE INVENTION

Aspects of the invention include systems, apparatuses, and designs to secure the electromagnetic impedance characteristics of a selected volume of one or more materials under test (MUTs) to determine its electromagnetic impedance characteristics and relate them to physical properties of that volume of the MUT.

Various embodiments include planar sensor arrays for use in determining characteristics of a material under test (MUT). The planar sensor arrays can include a set of electrodes positioned to enhance a depth and clarity of detection into the MUT. Some embodiments include an electromagnetic sensor array having: a first set of two rectilinear electrodes, positioned opposed to one another across a space; and a second set of two rectilinear electrodes, positioned opposed to one another across the space, the second set being off-set from the first set, wherein the first set and the second set are configured to detect an electromagnetic impedance of the MUT.

A first aspect includes various planar electrode sensor arrays meeting specified design criteria incorporated into systems and methods for communicating with various MUT. The systems include: a signal generator operably connected with the array of electrodes; the signal generator for transmitting oscillating electromagnetic field signals through the array of electrodes at a range of selected frequencies; a signal detector operatively connected to the array of electrodes; the array of electrodes in communication with the material under test; a signal comparison means operatively connected to the signal generator and the signal detector; and at least one computing device operably connected with the signal comparison means. The at least one computing device is configured to determine the electromagnetic impedance characteristics of selected volume of the MUT. The at least one computing device may also be configured to correlate the electromagnetic impedance characteristics of selected volumes of the MUT to physical properties of those volumes. The at least one computing device may also provide output to the user in various formats and transfer data files to another computer by various means.

A second aspect includes an electromagnetic sensor array having: a first set of two rectilinear electrodes, positioned opposed to one another across a space; and a second set of two rectilinear electrodes, positioned opposed to one another across the space, the second set being off-set from the first set, wherein the first set and the second set are configured to detect an electromagnetic impedance of a material under test (MUT).

A third aspect includes a system having: an array of electrodes for communicating with a surface and a subsurface beneath the surface, the array of electrodes including: a first set of two rectilinear electrodes, positioned opposed to one another across a space; and a second set of two rectilinear electrodes, positioned opposed to one another across the space, the second set being off-set from the first set; a signal generator operably connected with the array of electrodes; and at least one computing device operably connected with the signal generator and the array of electrodes, the at least one computing device configured to: instruct the signal generator to transmit a set of spectrographic signals from the array of electrodes into the surface and the subsurface; and obtain a return signal from the array of electrodes after the transmitting of the set of spectrographic signals to detect an electromagnetic impedance of at least one of the surface or the subsurface.

DETAILED DESCRIPTION

The following discussion expands on and improves the methodology disclosed in prior art to measure the impedance in a volume or volumes of the MUT using multiple electrodes arranged on a planar array in non-conducting communication with the MUT.

U.S. Pat. Nos. 5,900,736, 6,400,161, 6,414,497, and 6,677,763 present a two electrode sensor array as a means to evaluate the density of asphalt using electromagnetic impedance characteristics of the asphalt. The concentric two electrode sensor may also be classified electrically as a coplanar wave guide as noted in Patent Publication No. 2012/0013354. This prior art does not use any spectrographic or tomographic approaches but illustrates two electrode geometries for use with electromagnetic impedance measuring devices. U.S. Pat. No. 7,219,021 presents the use of a concentric coplanar electrode array with electromagnetic impedance spectroscopy to evaluate the density and moisture of soils. These electrode arrays are in non-conductive communication with the MUT. US Patent Publication Nos. 2009/0170756 and 2012/0130212 present a variation on the sensor geometry and mode of communication with the MUT with impedance spectroscopy and introduces a method of impedance tomography. The variation in the electrode sensor array moved from the concentric electrodes in U.S. Pat. Nos. 5,900,736 and 6,414,497 to a linear four-electrode array known as a Wenner array. The method of communication between the concentric electrode array and the linear array moved from a non-conductive communication to a conductive communication. U.S. Provisional Patent Application Nos. 61/647,848 and 61/703,488 present two different methods of evaluating a MUT with impedance spectroscopy and impedance tomography with linear electrode arrays in non-conductive communication the MUT.

The various embodiments of the electrode sensor arrays presented in this application provide improvements to the art in U.S. Pat. Nos. 5,900,736, 6,400,161, 6,414,497, 6,677,763, and 7,219,021 and US Patent Publication No. 2012/0013354 to secure electromagnetic impedance and electromagnetic impedance spectrographic characteristics of selected volumes of the MUT which may then correlate the impedance characteristics to physical properties of the selected volumes of the MUT.

As noted herein, the use of electromagnetic impedance measurement devices to secure physical properties of a material under test with a planar electrode sensor array have been identified in U.S. Pat. Nos. 5,900,736, 6,400,161, 6,414,497, and 7,219,024. The apparatuses described in U.S. Pat. Nos. 5,900,736, 6,414,497, and 7,219,024, use a planar concentric electrode array to secure data about a MUT. US Patent Publication No. 2012/0013354 also presents a planar concentric electrode array and terms it a "concentric coplanar capacitive sensor". The planar concentric electrode arrays fall under a class of electronics that is termed "coplanar wave guides." While there are a number of advantages in using the concentric electrode array, this array also has limitations. A first limitation is that the concentric electrode array is not readily conducive to providing tomographic information. The use of electromagnetic tomographic and spectrographic measurement devices, which have been identified in US Patent Publication Nos. 2009/0170756 and 2012/0130212, and U.S. Patent Application Nos. 61/647,848 and 61/703,488, address the issue of locating specified volumes within a MUT and characterizing that volume based upon its electromagnetic characteristics. A second limitation of the concentric electrode array is that the size of the electrode array limits the potential depth of evaluation into the MUT. In general, the maximum depth that can be evaluated is at best equal to one half of the sensor diameter, and in practice, the depth is even less.

Various embodiments disclosed herein include planar electrode arrays that address, among other things, the second limitation of the concentric electrode array noted herein. Various embodiments of the designs presented in US Patent Publication Nos. 2009/0170756 and 2012/0130212 and U.S. Provisional Patent Application Nos. 61/647,848 and 61/703, 488 address the first limitation of the concentric electrode array noted herein.

Various particular embodiments include an electromagnetic sensor array having: a first set of two rectilinear electrodes, positioned opposed to one another across a space; and a second set of two rectilinear electrodes, positioned opposed to one another across the space, the second set being off-set from the first set, wherein the first set and the second set are configured to detect an electromagnetic impedance of a material under test (MUT).

Various additional particular embodiments include a system having: an array of electrodes for communicating with a surface and a subsurface beneath the surface, the array of electrodes including: a first set of two rectilinear electrodes, positioned opposed to one another across a space; and a second set of two rectilinear electrodes, positioned opposed to one another across the space, the second set being off-set from the first set; a signal generator operably connected with the array of electrodes; and at least one computing device operably connected with the signal generator and the array of electrodes, the at least one computing device configured to: instruct the signal generator to transmit a set of spectrographic signals from the array of electrodes into the surface and the subsurface; and obtain a return signal from the array of electrodes after the transmitting of the set of spectrographic signals to detect an electromagnetic impedance of at least one of the surface or the subsurface.

As used herein, when referring to an off-set between pairs of (or individual) electrodes, it is understood that the term "off-set" can mean off-axis, that is, on a distinct axis from, but in some cases, within the same plane as, the reference element. In the case of sets of electrodes, a first set may define an axis, and a second set may be off-set from the first set by, e.g., 90 degrees. That is, the second set is positioned substantially similarly as the first set, but is rotated approximately 90 degrees from the first set (and in some cases, is within the same plane, e.g., into/out of the page).

According to various embodiments, a MUT can include any material capable of being characterized via one or more approaches shown and/or described herein. In various embodiments, a MUT includes an organic material such as a soil, or a biological material such as tissue, sub-tissue, organs, fluids, etc. A MUT can include synthetic, composite and/or other blended/modified materials. A MUT can also include elemental materials, as well as materials including impurities. It is understood that the teachings described according to the various embodiments herein can be applied to any MUT described herein, as well as other materials that can be characterized according to the approaches of the various embodiments.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Illustrations with respect to one or more implementations, alterations and/or modifications can be made to the illustrated examples without departing from the spirit and scope of the appended claims. In addition, while a particular feature may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

Figure 1:
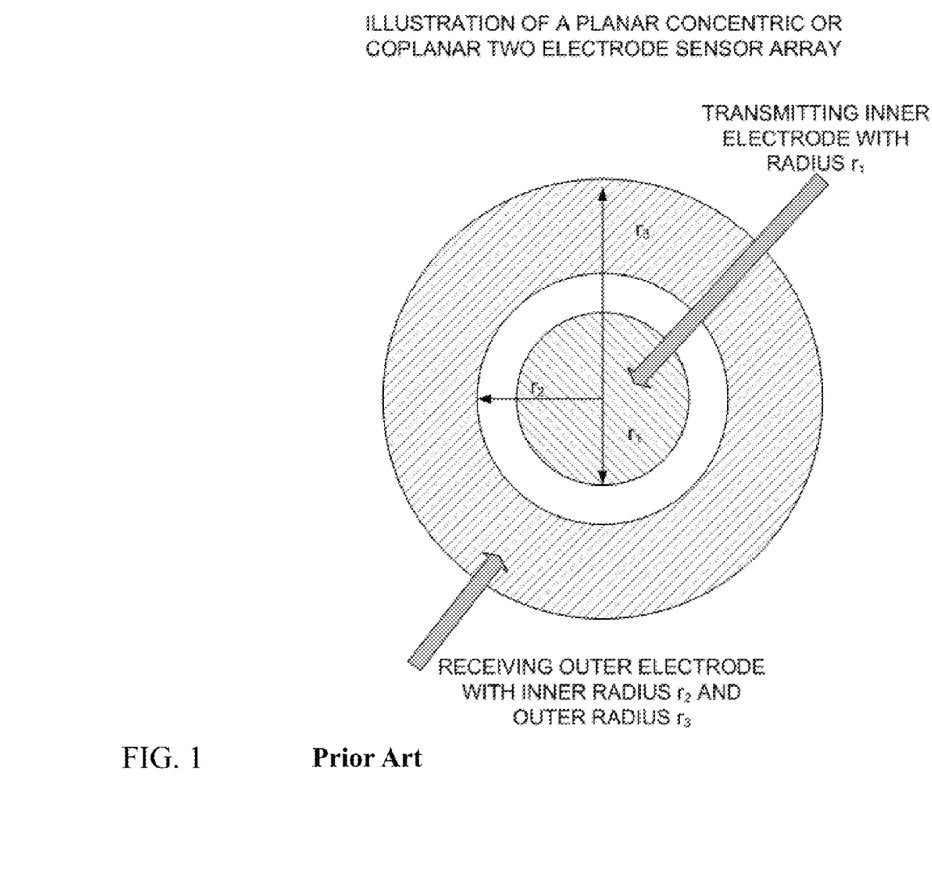
FIG. 1 shows an illustration of a planar concentric or coplanar two electrode array according to the prior art.

FIG. 1 shows a schematic depiction of a prior art two-electrode planar sensor in a concentric or coplanar configuration. As also established in the prior art, a concentric array of three electrodes in a planar configuration may be used to evaluate two volumes of the MUT to different depths. In these conventional approaches, the center electrode is always transmitting the probing electromagnetic signal at a single frequency or a range of frequencies, while only one of the outer electrode rings acts as a receiving electrode for the return signal from the MUT, as shown in the side, cross-sectional depiction in FIG. 2 of the prior art sensor in FIG. 1. Again, the electromagnetic waves are transmitted to the MUT through the electrodes in a non-conductive manner.

Figure 3:
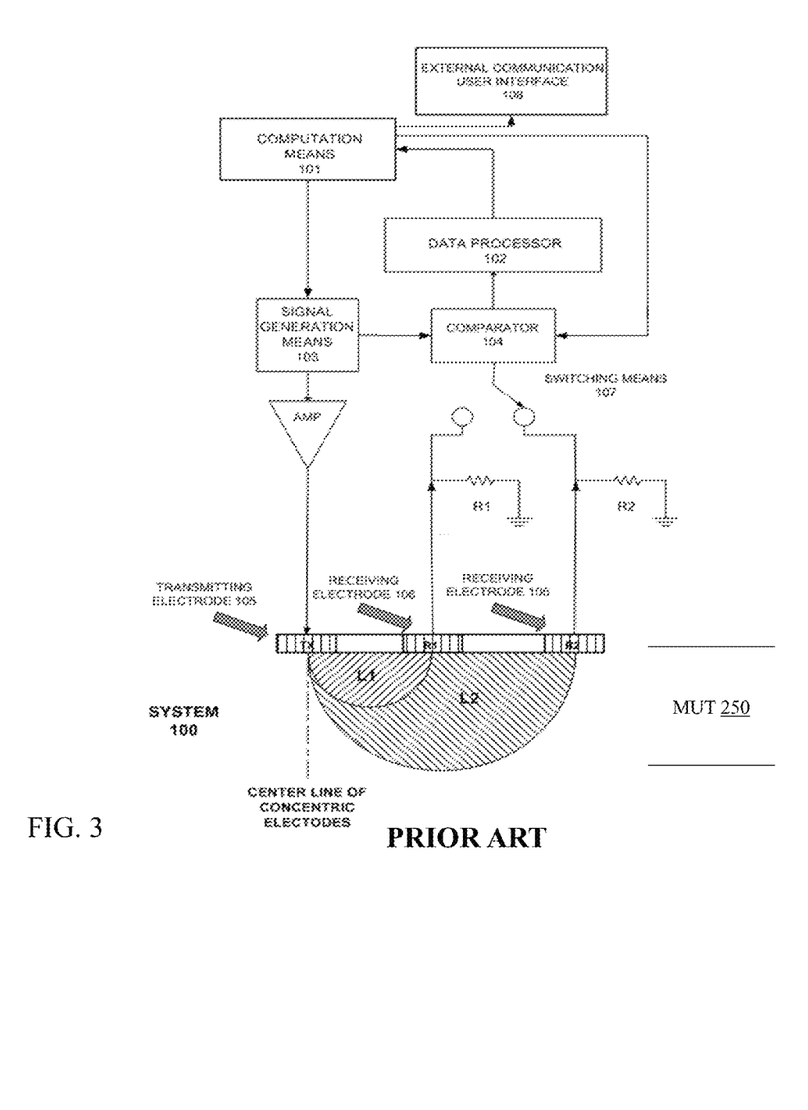
FIG. 3 shows an illustration of a measurement system for the electrode array in FIG. 2 according to prior art.

FIG. 3 presents a schematic depiction illustrating a prior art impedance sensor system 100, with three concentric electrodes (transmitting electrode 105, and receiving electrodes 106). The center electrode 105 is always the transmitting electrode and one of concentric electrodes 106 is selected to be the receiving electrode through switching means 107 as controlled by the computation means 101. A signal generator means 103, such as a DDS (Direct Digital Synthesizer) 102, provides an electromagnetic signal at a signal frequency or a range of frequencies as controlled by the computation means which is transmitted through the MUT 250 from electrode 105 to electrode 106. The signal from electrode 106 is compared to the transmitted signal in a comparator 104, to provide the impedance characteristics of the MUT 250 in volumes L1 or L2. The readings from the comparator 104 are then communicated to a data processor 102 and then to the comparator 104 or directly to the computation means 101. In the prior art impedance sensor system 100 illustrated in FIG. 3, the order/orientation of the transmitting electrode 105 and the receiving electrodes 106 are fixed. The computation means 101 can communicate with external data storage (e.g., via external communication user interface 108), computation means 101 or various methods of communication to the user as is well known in the art. Other means of providing and processing the electromagnetic signal are described in U.S. Patent Application Nos. 61/647,848, 61/703,408, and 61/784,363 (each of which is incorporated by reference herein in its entirety).

Conventional approaches have established that the depth of the measurement into the MUT 250 is defined by the spacing between the electrodes. Referring back to FIG. 2, the depth, $Z_1$, into the L1 volume of the MUT that the circular electrode R1 can measure is equal to 0.5Δ1. Similarly, the depth, $Z_2$, into L2 volume of the MUT that the circular electrode R2 can measure is equal to 0.5Δ2. The limitations in conventional measurement techniques, based upon the distance between electrodes, whether in concentric or other alternative arrangements, as discussed herein, either impact the size of the sensor array or are limited by the acceptable size of the sensor array for a test instrument for field use. That is, in some cases, the spacing required between adjacent electrodes in order to detect a desired depth may exceed the dimensions of the surface of the MUT to be measured, limiting either the depth or the type of MUT that can be measured.

Figure 4:
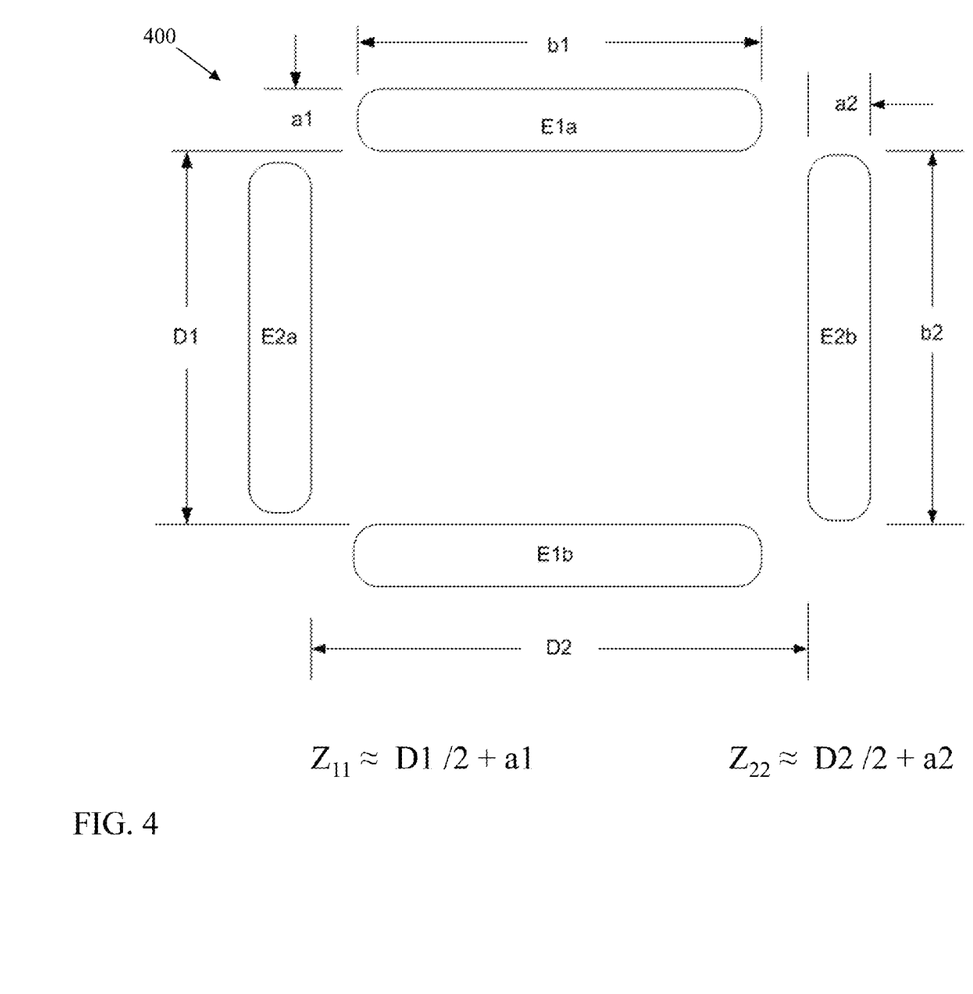
FIG. 4 shows an illustration of a four electrode planar array to evaluate a single volume of the MUT according to various embodiments.

FIG. 4 shows a schematic plan view of an electrode array 400 including a set of rectilinear electrodes and associated dimensions according to various embodiments. As shown in FIG. 4, the electrode array 400 includes two sets of rectilinear electrodes, E1a,b and E2a,b, that are spaced opposing each other. The electrodes E1, E2 can be spaced at a distance $D_{1,2}$. According to some embodiments, the electrodes E1, E2 are all of substantially equal size with a width, a, and a length, b. The depth, Z, which can be measured into a MUT (e.g., MUT 250), may be given by the following:

$$Z = \frac{(D+2a)}{2}$$

The electrodes E1a and E1b and the electrodes E2a and E2b may each be either a transmitting or receiving electrode. For example, E1a act as a transmitting electrode and E1b act as a receiving electrode, to make one measurement of the MUT volume (e.g., MUT 250). Then, successively, or at a different time, E1a can act as the receiving electrode and E1b can act as the transmitting electrode, to make another measurement of the same volume of the MUT. The same switching technique can be performed using electrode E2a and electrode E2b. The ability to switch each electrode between being either a transmitting or a receiving electrode allows a detection system to obtain a greater amount of data about the impedance characteristics of the volume of the MUT under inspection by measuring the same volume twice, when compared with conventional approaches. Readings between the electrodes may be conducted sequentially over a selected range of frequencies, or simultaneously over a range of frequencies where the frequencies for the E2 electrodes are staggered by an incremental frequency, $\epsilon$, from the frequencies transmitted to the E1 electrodes. For example, the E1 electrodes can operate at a frequency f and the electrodes E2 can operate at a frequency f$\pm\epsilon$.

Figure 2:
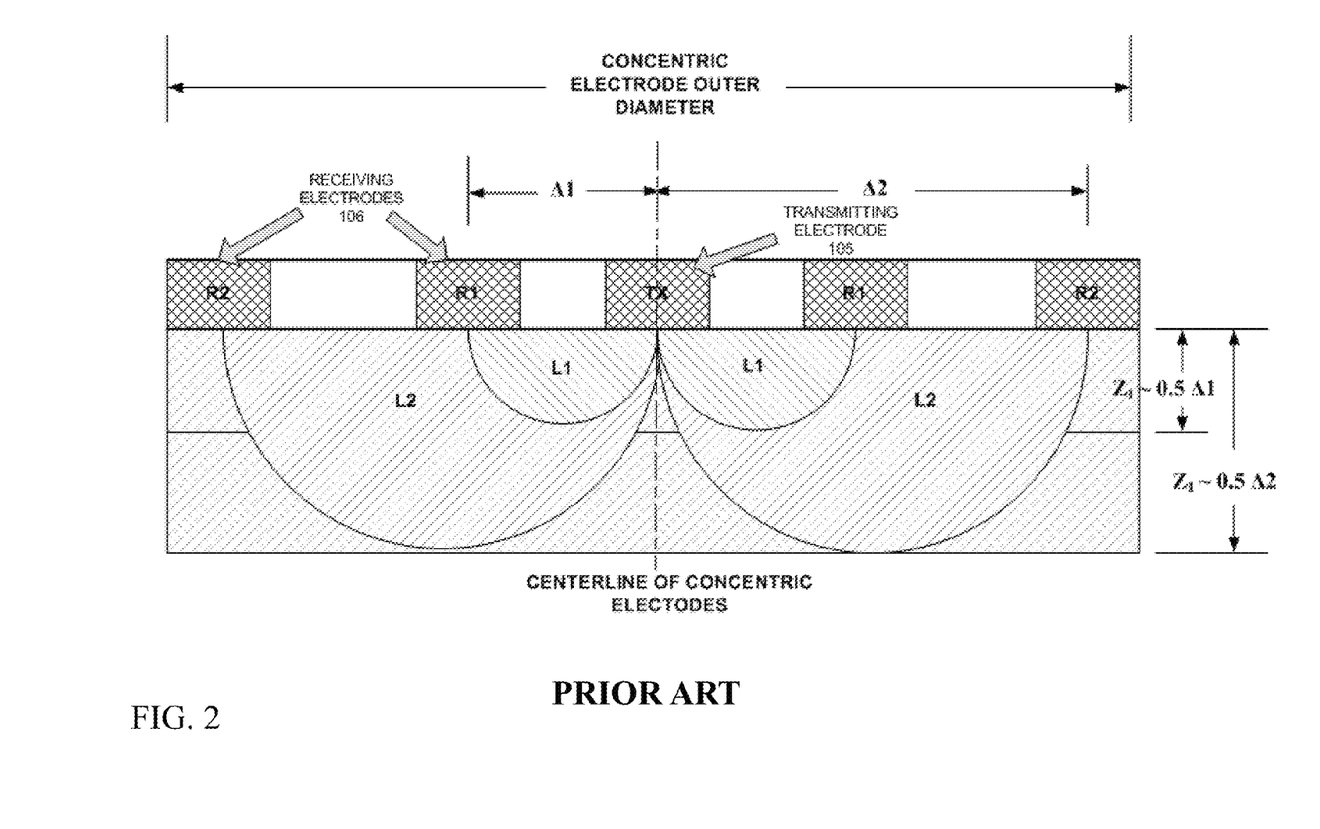
FIG. 2 shows an illustration of two concentric or coplanar two-electrode arrays to measure two separate volumes of the MUT according to prior art.
Figure 5:
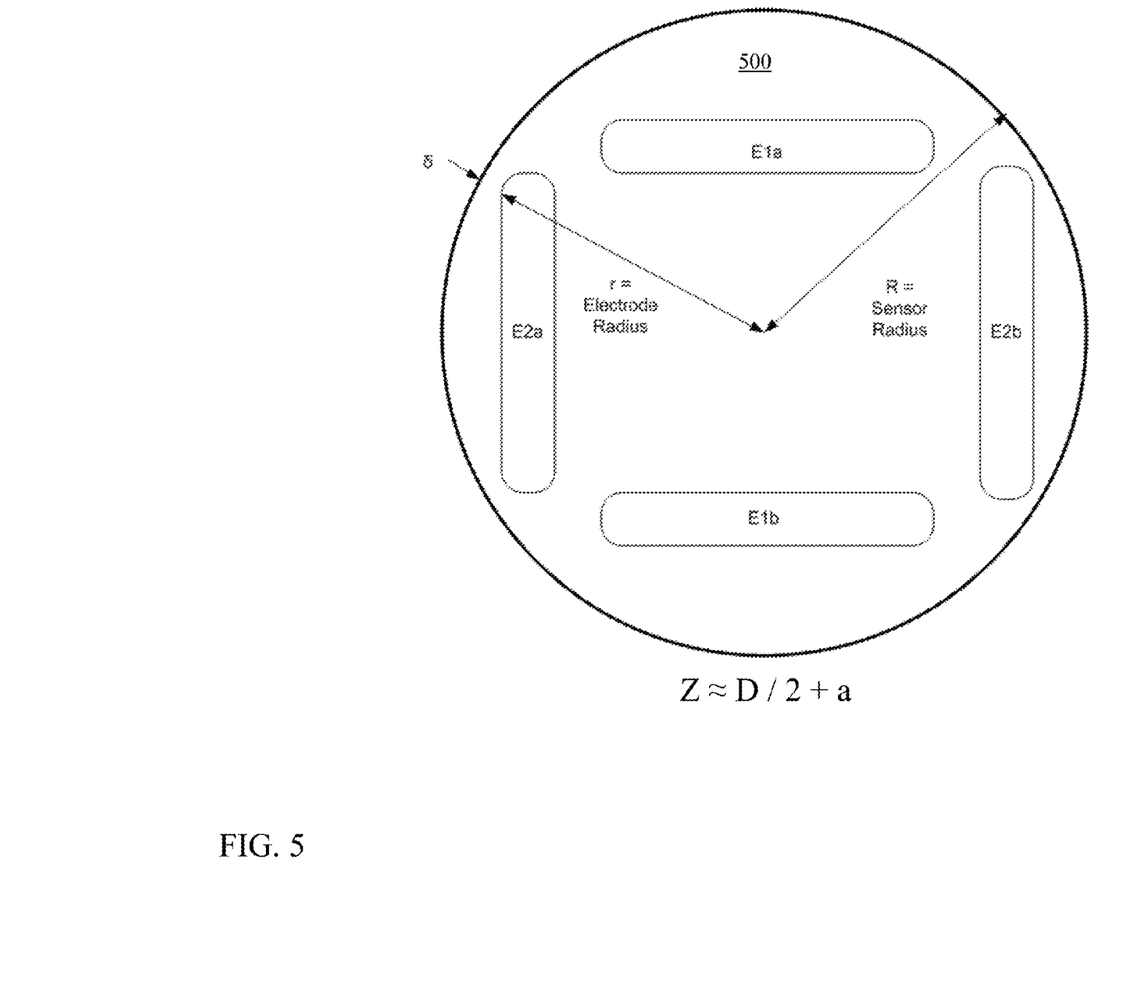
FIG. 5 shows an illustration of the arrangement of the planar arrays mounted on a circular support structure according to various embodiments.

The electrode array 400 shown can be configured to obtain spectrographic data about a volume of the MUT 250 that may be comparable to the spectrographic data obtainable by the concentric electrode arrangement of the prior art, however, the electrode array 400 can obtain spectrographic data about the MUT 250 at nearly twice the depth into the MUT 250 as the conventional electrode array (e.g., as shown in FIG. 2). FIG. 5 shows a schematic plan view of a substantially circular sensor 500 containing the electrode array 400 of FIG. 4. The equivalent radius of this electrode array 400, r, can be compared to that of the concentric array, $r_3$, in FIG. 1 as follows:

$$r = \sqrt{\left(\frac{D}{2}\right)^2 + Da + a^2 + \left(\frac{b}{2}\right)^2}$$

As noted with respect to FIG. 4, the electrodes E1, E2 can be spaced at a distance $D_{1,2}$, and according to some embodiments, the electrodes E1, E2 are all of substantially equal size with a width, a, and a length, b.

For various electromagnetic and mechanical reasons, the sensor plate (sensor 500) upon which (and/or within which) at least a portion of the electrodes (E1, E2) are mounted is larger than the value of the radius, r. If the incremental size is $\delta$ as shown in FIG. 5, the sensor plate radius, R, is given by the following:

$$R = \delta + r = \delta + \sqrt{\left(\frac{D}{2}\right)^2 + Da + a^2 + \left(\frac{b}{2}\right)^2}$$

where $\delta$ is the smallest distance between an electrode and the edge of the sensor as shown in FIG. 5.

Figure 6:
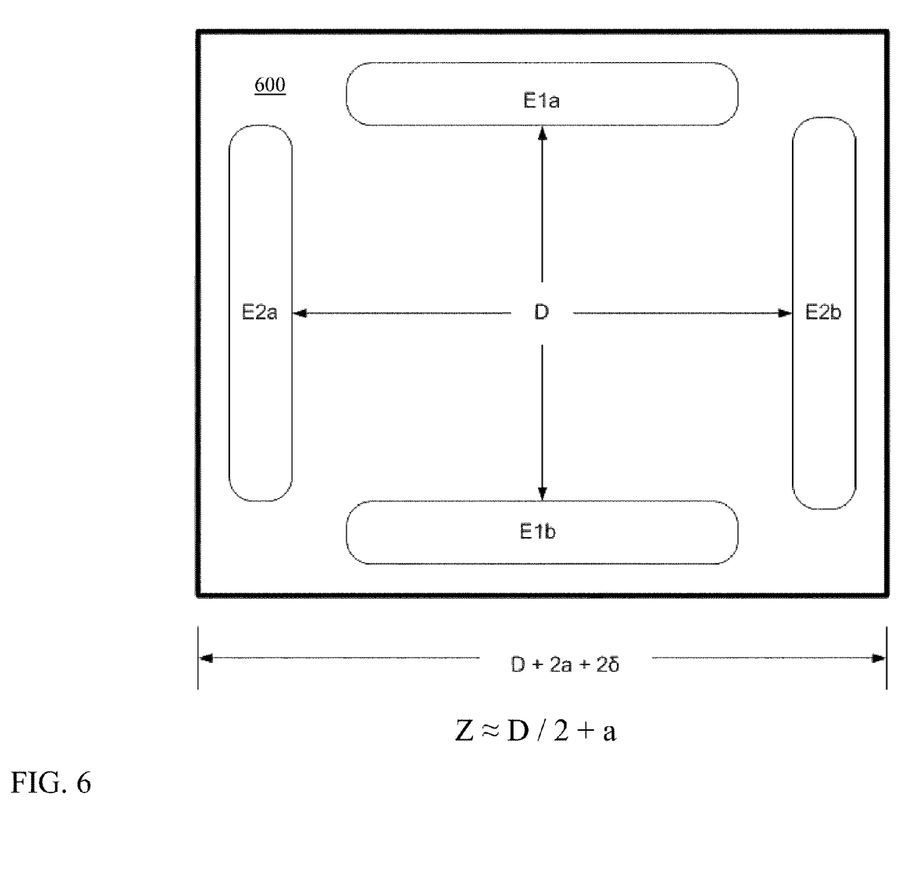
FIG. 6 shows an illustration of the arrangement of the planar arrays mounted on a square support structure according to various embodiments.

This sensor plate radius can be significant, as it defines the size of the field instrument carrying (housing) the sensor plate 500. In various additional embodiments, a sensor 600 including a rectilinear sensor plate, may take the form as shown in FIG. 6, that is, it may include a rectilinear plate (as compared with a substantially circular plate shown in FIG. 5).

Figure 7:
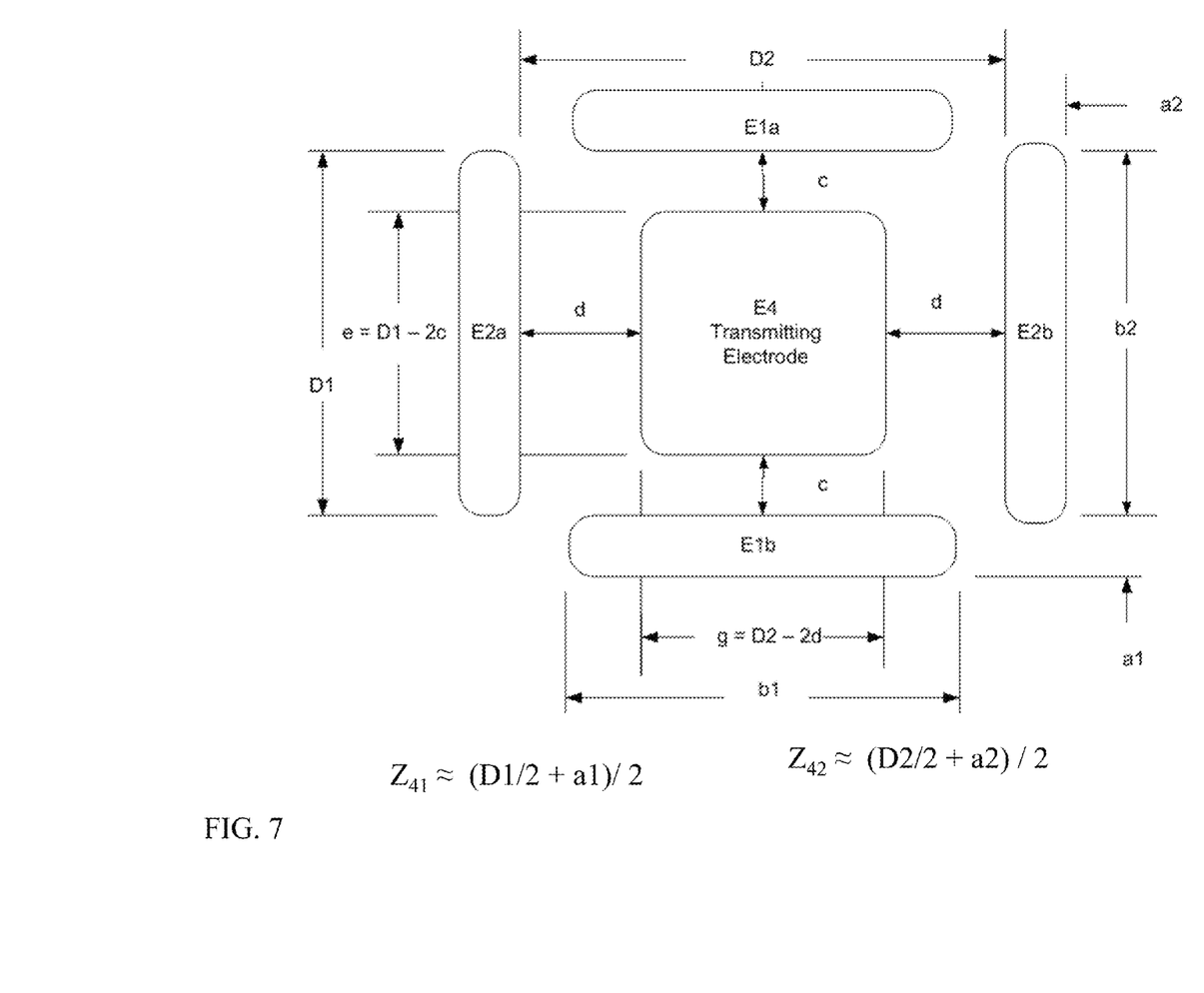
FIG. 7 shows an illustration of a five electrode planar array single transmitting electrode and two sets of receiving electrodes to evaluate two volumes of the MUT according to various embodiments.

In FIG. 7, a schematic plan view of a sensor array 700 is shown according various embodiments, the sensor array 700 including a variation of the geometry of the sensor array 400 in FIG. 4. The sensor array 700 is configured to determine characteristics of the MUT (via spectrography calculations) at two different depths into the MUT 250. In addition to the four electrodes (E1a, E1b, E2a, E2b) on the sides, a central electrode, E4, is incorporated in the design. In these embodiments, the central electrode E4 can be configured as a transmitting-only electrode, and the four side electrodes (E1a, E1b, E2a, E2b) can be configured as receiving-only electrodes. The transmissions may be made between E4 and E1a/E1b or E4 and E2a/E2b. In the illustration in FIG. 7, the measurement depth $Z_{41}$ is less than $Z_{42}$. The transmission at a selected frequency or frequency range may occur independently between either of the electrode combinations. An alternate approach as indicated in U.S. Provisional Patent Application No. 61/906,664 (hereby incorporated by reference in its entirety) is to operate both electrode combinations simultaneously with a staggering in the frequencies of the electrodes, where each transmitting electrode is operated at a different frequency, with a separation of $\epsilon$ Hz.

Figure 8:
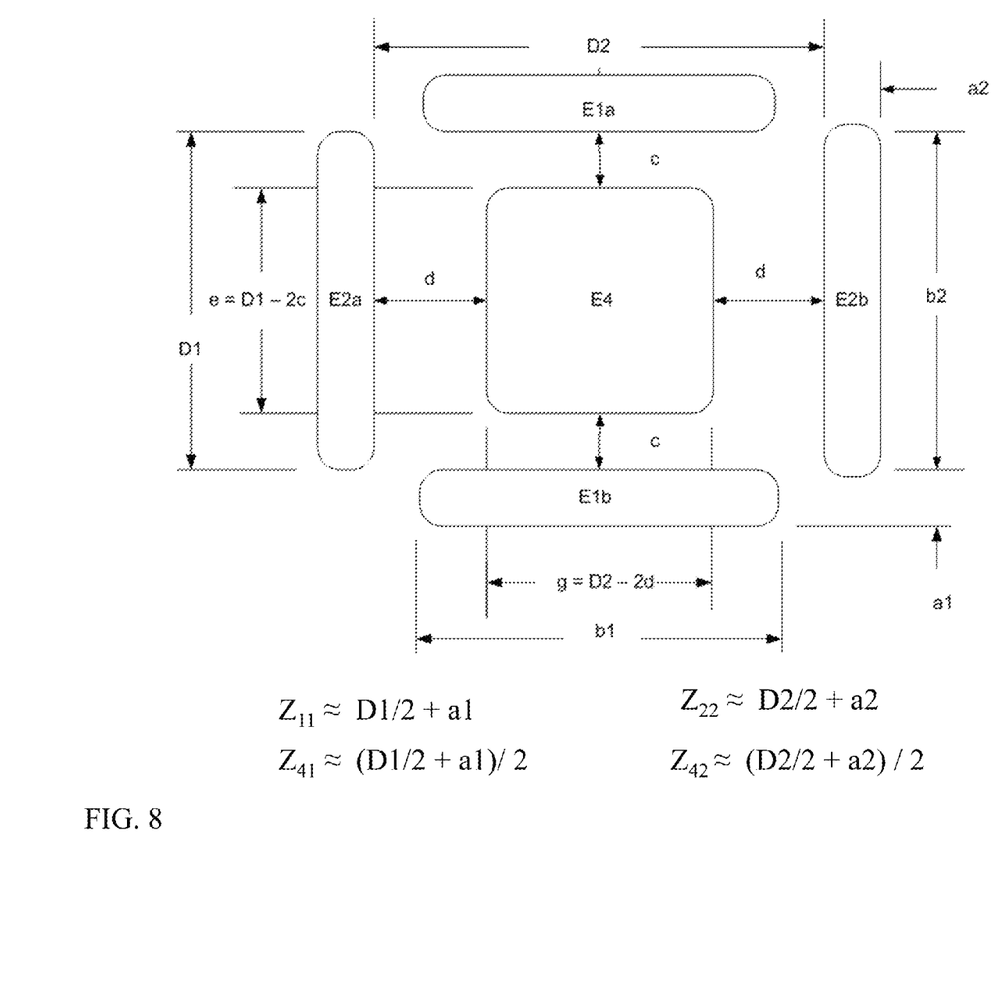
FIG. 8 shows an illustration of a combination of the functionality of the arrays in FIGS. 4 and 7 to evaluate three volumes of the MUT with a five electrode planar array according to various embodiments.

The array 700 shown in FIG. 7 may include the functionality of the array shown in FIG. 4, as illustrated in the schematic depiction of FIG. 8. That is, the array 700 including a central electrode E4 may be configured to act with or without the central electrode E4 to determine characteristics of one or more MUTs at one or more depths. The embodiment shown in FIG. 8 permits the measurement of four different depths into the MUT, or variations of the available depth selections in different MUTs. For example, electrode arrays E4-E1a/E1b and E4-E2a/E2b may be applied to measuring asphalt, and electrodes E1a-E1b and E2a-E2b may be applied to measuring soils.

Figure 9:
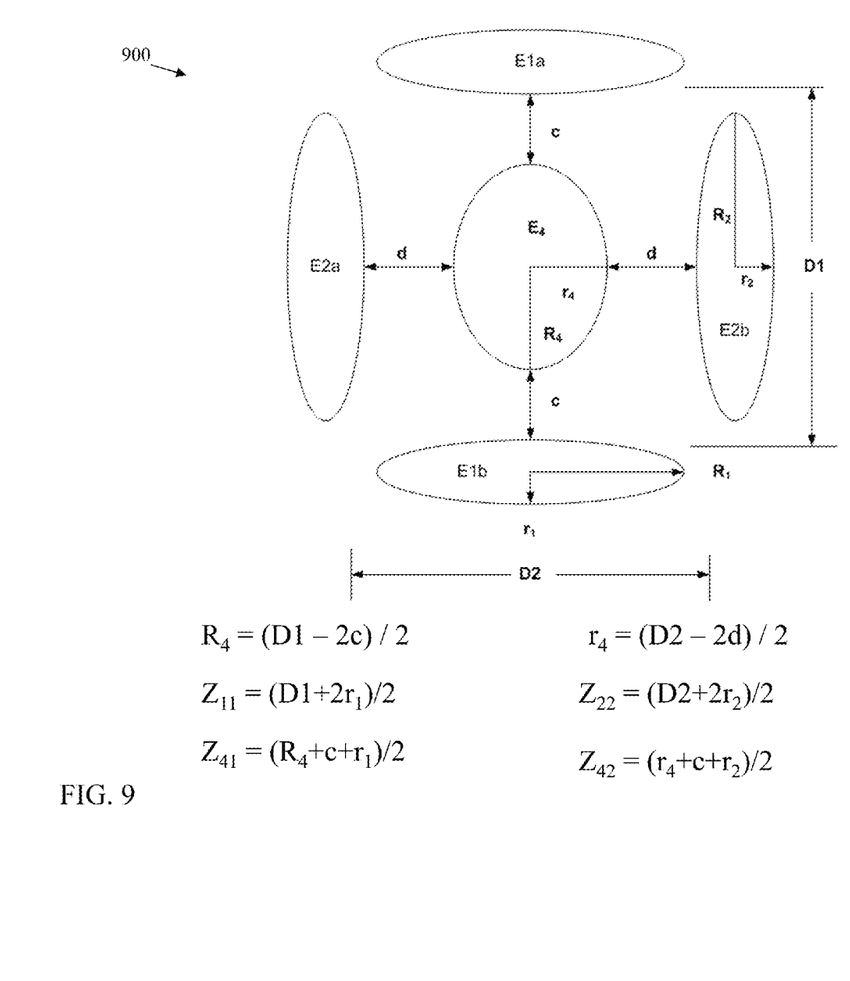
FIG. 9 shows an illustration of the electrode array in FIG. 8 with elliptical electrodes according to various embodiments.

The design of the electrodes in arrays 400, 500, 600 and 700 can allow for determination of characteristics of various forms of MUT, at various depths, to a greater extent than conventional arrays. In some particular embodiments, characteristics of the arrays 400, 500, 600, 700 can significantly impact their effectiveness in determining characteristic of a MUT. In some cases, the electrodes in each array will not have any sharp corners/edges or points, as these features tend to focus the field lines and may distort the flow of the electromagnetic field through the MUT 250 (causing erroneous measurements). The electrodes in arrays 400, 500, 600 and 700 are shaped as rectangles with rounded corners. An alternative design is shown in the array 900 in FIG. 9, where the electrodes are ellipsoids. Other similar designs are also possible, as will become evident to those having skill in the art.

A second design criterion according various embodiments can include the area of the electrodes (e.g., in arrays 400, 500, 600, 700, 900). In various embodiments, the area of the receiving electrodes is at least substantially equal to that of the transmitting electrode. Thus, referring to arrays 400, 500, 600 and 700, the area of electrodes are as follows:

Area E1a=Area E1b
Area E2a=Area E2b
Area E4<=Area E1a+E1b
Area E4<=Area E2a+E2b

Various approaches described allow for determining a physical property of a sub-voxel or a number of sub-voxels of the MUT 250. In various embodiments, a number of measurements of the physical property(ies) of interest are measured by conventional means and correlated with the measured variations of the measured complex impedance using the arrays/systems/approaches described herein. In various embodiments, the number of measurements can be sufficiently large such that the resulting correlation is statistically significant. The impedance measurements can be made with the same type of array that will be used to inspect unknown MUTs. The measurements may also be made over a range of frequencies. Further embodiments include a method of developing an algorithm to correlate the physical property to the measured impedance, which may use any number of well known correlation methods such as analysis of variations (ANOVA), neural networks, and multiple regressions. A determination as to which process, impedance characteristic and frequency may ensure that the best fit may be made by selection of the one that provides the most statistically significant results.

Figure 10:
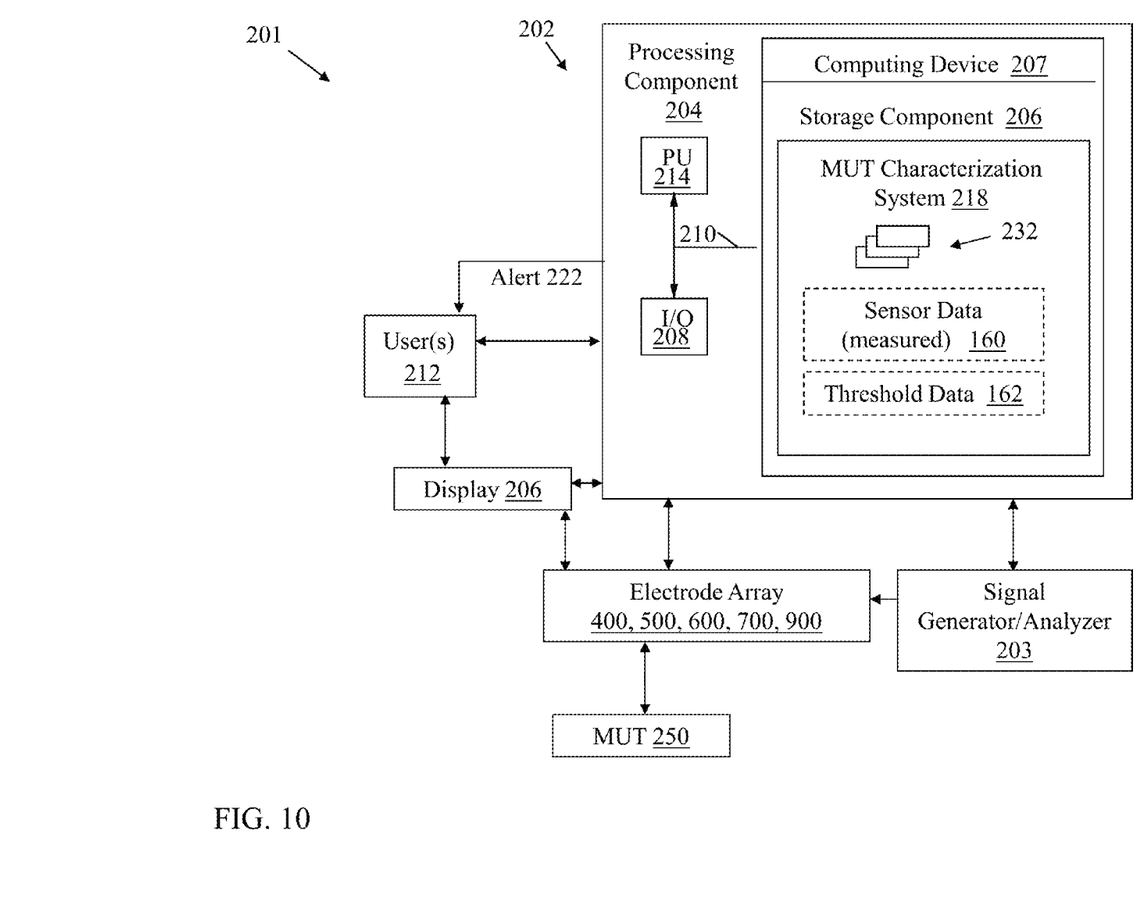
FIG. 10 shows an environment for characterizing a MUT according to various embodiments.

FIG. 10 shows a schematic depiction of a system 201 for characterizing select volumes of a material under test (MUT) 250 by performing processes described herein with respect to various embodiments. To this extent, the system 201 includes a computer system 202 that can perform one or more processes described herein in order to control operation of a sensor array system (e.g., electrode array 400, 500, 600, 700 and/or 900, such as those shown and described with reference to FIGS. 4-9), a signal generator/analyzer 203, and/or a display 206. In particular, the computer system 202 is shown as including a MUT characterization system 218, which makes computer system 202 operable to characterize a MUT (including a surface/subsurface) by performing any/all of the processes described herein and implementing any/all of the embodiments described herein.

The computer system 202 is shown including computing device 207, which can include a processing component 204 (e.g., one or more processors), a storage component 206 (e.g., a storage hierarchy), an input/output (I/O) component 208 (e.g., one or more I/O interfaces and/or devices), and a communications pathway 210. In general, the processing component 204 executes program code, such as the MUT characterization system 218, which is at least partially fixed in the storage component 206. While executing program code, the processing component 204 can process data, which can result in reading and/or writing transformed data from/to the storage component 206 and/or the I/O component 208 for further processing. The pathway 210 provides a communications link between each of the components in the computer system 202. The I/O component 208 can comprise one or more human I/O devices, which enable a user (e.g., a human and/or computerized user) 212 to interact with the computer system 202 and/or one or more communications devices to enable the system user 212 to communicate with the computer system 202 using any type of communications link. To this extent, the MUT characterization system 218 can manage a set of interfaces (e.g., graphical user interface(s), application program interface, etc.) that enable human and/or system users 212 to interact with the MUT characterization system 218. Further, the MUT characterization system 218 can manage (e.g., store, retrieve, create, manipulate, organize, present, etc.) data, such as sensor data 160 and/or threshold data 162 using any solution. It is understood that the sensor data 160 can include data obtained by the sensor array 200 about the MUT 250. Threshold data 162 can include data representing one or more thresholds used to determine a characteristic of the MUT 250. That is, the threshold data 162 can be based upon predetermined conditions which account for a threshold level of spectrographic differential between the output signals and the return signals. The MUT characterization system 218 can additionally communicate with the electrode array 200, signal generator/analyzer 203, user 112 and/or display 106, e.g., via wireless and/or hardwired means.

In any event, the computer system 202 can comprise one or more general purpose computing articles of manufacture (e.g., computing devices) capable of executing program code, such as the MUT characterization system 218, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the MUT characterization system 218 can be embodied as any combination of system software and/or application software. It is further understood that the MUT characterization system 218 can be implemented in a cloud-based computing environment, where one or more processes are performed at distinct computing devices (e.g., a plurality of computing devices 207), where one or more of those distinct computing devices may contain only some of the components shown and described with respect to the computing device 207 of FIG. 19.

Further, the MUT characterization system 218 can be implemented using a set of modules 232. In this case, a module 232 can enable the computer system 202 to perform a set of tasks used by the MUT characterization system 218, and can be separately developed and/or implemented apart from other portions of the MUT characterization system 218. As used herein, the term "component" means any configuration of hardware, with or without software, which implements the functionality described in conjunction therewith using any solution, while the term "module" means program code that enables the computer system 202 to implement the functionality described in conjunction therewith using any solution. When fixed in a storage component 206 of a computer system 202 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 202.

When the computer system 202 comprises multiple computing devices, each computing device may have only a portion of MUT characterization system 218 fixed thereon (e.g., one or more modules 232). However, it is understood that the computer system 202 and MUT characterization system 218 are only representative of various possible equivalent computer systems that may perform a process described herein. To this extent, in other embodiments, the functionality provided by the computer system 202 and MUT characterization system 218 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 202 includes multiple computing devices, the computing devices can communicate over any type of communications link. Further, while performing a process described herein, the computer system 202 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 202 can obtain or provide data, such as sensor data 160 and/or threshold data 162 using any solution. The computer system 202 can generate sensor data 260 and/or threshold data 262, from one or more data stores, receive sensor data 260 and/or threshold data 262, from another system such as the electrode array 200, signal generator/analyzer 203, user 212 and/or display 206, send sensor data 160 and/or threshold optical data 162 to another system, etc.

While shown and described herein as a method and system for characterizing an MUT (including, e.g., surface/subsurface), it is understood that aspects of the invention further provide various alternative embodiments. For example, in one embodiment, the invention provides a computer program fixed in at least one computer-readable medium, which when executed, enables a computer system to detect and characterize at least a portion of an MUT. To this extent, the computer-readable medium includes program code, such as the MUT characterization system 218 (FIG. 10), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the MUT characterization system 218 (FIG. 10), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for characterizing a MUT 250. In this case, a computer system, such as the computer system 202 (FIG. 10), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the invention, including, e.g., the MUT characterization system 218, is to control operation of an electrode array 400, 500, 600, 700 and/or 900, signal generator/analyzer 203, user 212 and/or display 206 to characterize at least a portion of a MUT in one of the various manners described and illustrated herein.

As described herein, various aspects of the invention can include computer implemented methods, systems and computer program products for performing a series of functions. In some cases, as shown in FIG. 10, a system 201 is described which includes an array of electrodes 200 for communicating (conductively or non-conductively) with a surface and a subsurface beneath the surface of MUT 250. As described herein, the array of electrodes 200 can be configured in a plurality of distinct ways to detect, and potentially determine the characteristics of, an MUT 250. The system 201 can further include a signal generator (in some cases including an analyzer) 203 operably connected (e.g., hard-wired) with the array of electrodes 400, 500, 600, 700, 900. The system 201 can further include at least one computing device 207 operably connected with the signal generator 203 (e.g., wirelessly and/or hard-wired) and the array of electrodes 200 (e.g., wirelessly and/or hard-wired, or simply via common connection with the signal generator).

For the purpose of promoting an understanding of the principals of the invention, reference has been made to the embodiments as illustrated in the drawings and specific language will be used to describe the same. It will nevertheless be understood that no limitation of the scope of the invention is thereby intended, such alterations and further modifications in the illustrated device and such further applications of the principal of the invention as illustrated therein being contemplated as would normally occur to one skilled in the art to which the invention relates.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The description of the principals of the invention uses specific illustrations of electronic component functions. These functions may be separated into multiple electronic components or they may be integrated into fewer electronic components to accomplish the same functionality as would normally occur to one skilled in the art to which the invention relates and to the availability and development of electronic components which perform the identified functions. Changes in the specific electronic components may result in changes in the circuits and logic flow as would normally occur to one skilled in the art to accomplish the same functionality.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It is further understood that the terms "front" and "back" are not intended to be limiting and are intended to be interchangeable where appropriate.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
an array of electrodes for communicating with a surface and a subsurface beneath the surface, the array of electrodes including:
a first set of two rectilinear electrodes, positioned opposed to one another across a space;
a second set of two rectilinear electrodes, positioned opposed to one another across the space, the second set being off-set from the first set; and
a central electrode located within the space between the first set of two rectilinear electrodes and the second set of two rectilinear electrodes;
a signal generator operably connected with the array of electrodes; and
at least one computing device operably connected with the signal generator and the array of electrodes, the at least one computing device configured to:
instruct the signal generator to transmit a set of spectrographic signals from the array of electrodes into the surface and the subsurface; and
obtain a return signal from the array of electrodes after the transmitting of the set of spectrographic signals to detect an electromagnetic impedance of at least one of the surface or the subsurface,
wherein each of the two rectilinear electrodes in the first set and each of the two rectilinear electrodes in the second set is configured to perform at least one of transmitting the set of spectrographic signals into at least one of the surface or the subsurface or receiving the return signal from the at least one of the surface or the subsurface,
wherein each of the two rectilinear electrodes in the first set and each of the two rectilinear electrodes in the second set is configured to switch between the at least one of the transmitting of the set of spectrographic signals into the at least one of the surface or the subsurface or the receiving of the return signal from the at least one of the surface or the subsurface.

2. The system of claim 1, wherein the array of electrodes further includes a body housing the first set of two rectilinear electrodes and the second set of two rectilinear electrodes.

3. The system of claim 2, wherein the array of electrodes has an equivalent radius defined as:

$$r = \sqrt{\left(\frac{D}{2}\right)^2 + Da + a^2 + \left(\frac{b}{2}\right)^2}$$

wherein $D_{1,2}$=a spacing between electrodes in the first set or the second set, a=a width of each electrode and b=a length of each electrode.

4. The system of claim 3, wherein a body of the array of electrodes has a radius, R, defined according to:

$$R = \delta + r = \delta + \sqrt{\left(\frac{D}{2}\right)^2 + Da + a^2 + \left(\frac{b}{2}\right)^2}$$

wherein δ is the smallest distance between an electrode and an edge of the array of electrodes.

5. The system of claim 1, wherein the two rectilinear electrodes in the first set and the two rectilinear electrodes in the second set all have a size including a width (a) and wherein each of the two rectilinear electrodes in the first set and the two rectilinear electrodes in the second set are spaced apart from each other within the same set by a distance (D), wherein the first set and the second set are configured to detect an electromagnetic impedance of the subsurface at a depth (Z) according to:

$$Z = \frac{(D+2a)}{2}.$$

6. The system of claim 1, wherein the central electrode is configured as a transmitting-only electrode, and wherein the first set of two rectilinear electrodes and the second set of two rectilinear electrodes are both configured as receiving-only electrodes.

7. The system of claim 1, wherein the central electrode, combined with the first set and the second set, are configured to detect the electromagnetic impedance of the at least one of the surface or the subsurface at two distinct depths in the at least one of the surface or the subsurface.

8. The sensor array of claim 1, wherein the central electrode, combined with the first set and the second set, are configured to detect the electromagnetic impedance of the at least one of the surface or the subsurface at four distinct depths in the at least one of the surface or the subsurface.

9. The system of claim 1, wherein the central electrode is configured to transmit a first electromagnetic signal at a first frequency through the at least one of the surface or the subsurface, and the first set of two rectilinear electrodes is configured to receive the first electromagnetic signal after transmission through the at least one of the surface or the subsurface, and wherein the central electrode is configured to transmit a second electromagnetic signal at a second frequency, distinct from the first frequency, through the at least one of the surface or the subsurface, and the second set of two rectilinear electrodes is configured to receive the second electromagnetic signal after transmission through the at least one of the surface or the subsurface.

10. The system of claim 9, wherein the second frequency is staggered from the first frequency by a frequency increment of $\epsilon$ Hz.

11. The system of claim 10, wherein the first frequency and the second frequency are transmitted substantially simultaneously.

12. A system comprising:
    an array of electrodes for communicating with a surface and a subsurface beneath the surface, the array of electrodes including:
        a first set of two rectilinear electrodes, positioned opposed to one another across a space; and
        a second set of two rectilinear electrodes, positioned opposed to one another across the space, the second set being off-set from the first set;
    a signal generator operably connected with the array of electrodes; and
    at least one computing device operably connected with the signal generator and the array of electrodes, the at least one computing device configured to:
        instruct the signal generator to transmit a set of spectrographic signals from the array of electrodes into the surface and the subsurface; and
        obtain a return signal from the array of electrodes after the transmitting of the set of spectrographic signals to detect an electromagnetic impedance of at least one of the surface or the subsurface,
    wherein the first set of two rectilinear electrodes and the second set of two rectilinear electrodes are configured to detect an electromagnetic impedance of the at least one of the surface or the subsurface by transmitting the spectrographic signals into the at least one of the surface or the subsurface over a selected range of frequencies, either sequentially or simultaneously, wherein the first set of two rectilinear electrodes are configured to transmit a first set of spectrographic signals into the at least one of the surface or the subsurface, and the second set of two rectilinear electrodes are configured to transmit a second set of spectrographic signals into the at least one of the surface or the subsurface, wherein the second set of signals is staggered from the first set of signals by a frequency increment of $\epsilon$ Hz.

\* \* \* \* \*